United States Patent [19]

Crenshaw et al.

[11] Patent Number: 4,588,457
[45] Date of Patent: May 13, 1986

[54] TWO-PLY NONWOVEN FABRIC LAMINATE

[75] Inventors: Susan L. H. Crenshaw, Memphis, Tenn.; Neal L. Schlintz, Newcastle upon Tyne, England; Danny R. Moore, Germantown, Tenn.

[73] Assignee: The Procter & Gamble Company, Cincinnati, Ohio

[21] Appl. No.: 762,095

[22] Filed: Aug. 2, 1985

Related U.S. Application Data

[62] Division of Ser. No. 474,417, Mar. 11, 1983.

[51] Int. Cl.$^4$ ............................................. B29J 5/00
[52] U.S. Cl. ........................................ 156/62.8; 156/296
[58] Field of Search ............................... 156/62.8, 296

[56] References Cited

U.S. PATENT DOCUMENTS

| | | | |
|---|---|---|---|
| 2,954,817 | 10/1960 | Havemann | 156/169 |
| 3,072,511 | 1/1963 | Harwood | 154/46 |
| 3,327,708 | 6/1967 | Sokolowski | 128/156 |
| 3,388,028 | 6/1968 | Alexander | 161/156 |
| 3,484,330 | 12/1969 | Sokolowski et al. | 16/59 |
| 3,546,056 | 12/1970 | Thomas | 161/57 |
| 3,600,262 | 8/1971 | Frank | 161/79 |
| 3,615,976 | 10/1971 | Endres et al. | 156/83 |
| 3,629,047 | 12/1971 | Davison | 161/57 |
| 3,639,199 | 2/1972 | Brandts et al. | 161/57 |
| 3,673,052 | 6/1972 | Small et al. | 156/164 |
| 3,674,594 | 7/1972 | Persson | 156/299 |
| 3,695,985 | 10/1972 | Brock et al. | 161/129 |
| 3,753,844 | 8/1973 | Braun | 161/57 |
| 3,765,997 | 10/1973 | Dunning | 161/141 |
| 3,770,562 | 11/1973 | Newman | 428/287 |
| 3,788,936 | 1/1974 | Brock et al. | 161/148 |
| 3,793,133 | 2/1974 | Beaudoin et al. | 161/148 |
| 3,794,537 | 2/1974 | Rahmes | 156/62.8 |
| 3,809,077 | 5/1974 | Hansen | 128/132 |
| 3,862,877 | 1/1975 | Camden | 161/57 |
| 3,870,592 | 3/1975 | Brock et al. | 161/148 |
| 3,900,632 | 8/1975 | Robinson | 428/196 |
| 4,001,472 | 1/1977 | Thomas et al. | 428/109 |
| 4,113,911 | 9/1978 | LaFitte et al. | 428/284 |
| 4,142,017 | 2/1979 | Blackburn et al. | 428/284 |
| 4,194,939 | 3/1980 | Perry | 156/254 |
| 4,196,245 | 4/1980 | Kitson et al. | 428/198 |

FOREIGN PATENT DOCUMENTS

1200235  7/1970  United Kingdom ............... 154/40

Primary Examiner—James J. Bell
Attorney, Agent, or Firm—John M. Pollaro; Fredrick H. Braun; Richard C. Witte

[57] ABSTRACT

A two-ply nonwoven fabric laminate comprises a first-ply of synthetic fibrous nonwoven material having an outer surface, an inner surface, and a thickness, and having a basis weight of from about 10 g/m$^2$ to about 50 g/m$^2$; and a second ply of fibrous nonwoven material having an outer surface, an inner surface, and a thickness, and having a basis weight of from about 10 g/m$^2$ to about 50 g/m$^2$. The inner surfaces of the first and second plies are adhered at their interface by a flexible, soft latex binder. The binder is adhered to substantially all fibers exposed on the inner surfaces of the first and second plies. The binder is present in the first ply from its inner surface to a depth of from about 20% to about 80% of its thickness, and is present in the second ply from its inner surface to a depth of from about 20% to about 80% of its thickness.

22 Claims, 3 Drawing Figures

TWO-PLY NONWOVEN FABRIC LAMINATE

This is a division of application Ser. No. 474,417, filed on Mar. 11, 1983.

TECHNICAL FIELD

The invention relates to nonwoven fabric laminates, and specifically to two-ply nonwoven fabric laminates and a process for making such laminates.

BACKGROUND ART

The two-ply nonwoven fabric laminates of the present invention are lightweight fabric laminates which are relatively high in both air porosity and liquid strike-through resistance. This combination of high liquid strikethrough resistance and high air porosity can be obtained in nonwoven fabric laminates of the present invention having substantially lower basis weight than other nonwoven fabric laminates having comparable air porosity and liquid strikethrough resistance properties.

The nonwoven fabric laminates of the present invention have many applications and, in fact, may be used wherever their liquid strikethrough resistance/air porosity/basis weight relationships would be advantageous. For example, the nonwoven fabric laminates could be used in the manufacture of clothing where a barrier to liquid strikethrough is desired, e.g. laboratory costs, artists' smocks, hospital scrub clothes, or the like.

The primary use envisioned for the two-ply nonwoven fabric laminates of the present invention is for disposable surgical gowns and drapes. The laminates are especially suitable for surgical gowns are high liquid strikethrough resistance, is needed to prevent liquid-borne contaminates from passing through the gown fabric, but where fabric light in weight and having high air porosity is important for the comfort of the wearer. The two-ply nonwoven fabric laminates of the present invention are particularly suitable for use in the manufacture of disposable zoned surgical gowns. Such gowns have zones of extra water repellency or water impermeability in areas where contact with contaminated fluids is most likely to occur, especially the upper gown front and the lower sleeves of the gown.

Prior art workers have developed a number of fabrics for use in surgical gowns, surgical drapes and the like. There are a number of critical physical properties which are sought for such fabrics. These properties include: essentially no particulate discharge (lint or the like), essentially no abrasion or pilling, high liquid strikethrough resistance, high air porosity, adequate strength and tear resistance, lightweight, and cloth-like aesthetic properties. Prior art workers have found that it is necessary to aim for the best possible tradeoff among at least some of these properties because they tend to work against each other. A good example of this is air porosity on the one hand and liquid strikethrough resistance on the other. Another example is the weight of the fabric laminate and strength and tear resistance.

In producing fabric laminates for disposable products, it is necessary to strive for the least expensive laminates which provide the properties listed above, so that such products can be affordable. No single nonwoven material has been discovered which alone can provide all the desired properties listed above. Therefore, laminates of two or more materials have been combined in order to achieve a better balance of such properties. For economic reasons, it is generally desirable to have the fewest plies of material possible, while retaining the desired properties of such laminates, in order to minimize both the material and processing costs. For such economic reasons, a two-ply nonwoven fabric laminate having the above properties is highly desirable.

Exemplary prior art references which disclose two-ply nonwoven fabric laminates are disclosed in the following U.S. Pat. Nos. 3,327,708 issued to Sokolowski on June 27, 1967; 3,615,976 issued to Endres & Lewis on Oct. 26, 1971; 3,674,594 issued to Persson on July 4, 1972; 3,695,985 issued to Brock & Thomas on Oct. 3, 1972; 3,753,844 issued to Braun on Aug. 21, 1973; 3,788,936 issued to Brock, Hansen & Wilson on Jan. 29, 1974; 3,793,133 issued to Beaudoin, Brock & Minshell on Feb. 19, 1974; 3,870,592 issued to Brock & Hudson on Mar. 11, 1975; 3,900,632 issued to Robinson on Aug. 19, 1975; 3,770,562 issued to Newman on Nov. 6, 1973; and 3,809,077 issued to Hansen on May 7, 1974. Other U.S. patents which disclose disposable nonwoven fabric laminates include U.S. Pat. Nos. 3,072,511 issued to Harwood on Jan. 8, 1963; 3,600,262 issued to Frank on Aug. 17, 1971; 3,629,047 issued to Davison on Dec. 21, 1971; 3,862,877 issued to Camden on Jan. 29, 1975; 4,113,911 issued to LaFitte & Camden on Sept. 12, 1978; 4,142,017 issued to Blackburn & Goodwin on Feb. 27, 1979; and 4,196,245 issued to Kitson, Gilbert & Israel on Apr. 1, 1980. Many of the aforementioned patents also disclose processes for producing nonwoven fabric laminates; such a process is also disclosed in U.S. Pat. No. 2,954,817 issued to Havemann on Oct. 4, 1960.

SUMMARY OF THE INVENTION

It is an object of the present invention to provide a novel two-ply nonwoven fabric laminate.

It is a further object of the invention to provide such a laminate having relatively high air porosity and liquid strikethrough resistance in a laminate having a relatively low basis weight.

It is also an object of this invention to provide such a laminate having adequate tensile strength and tear resistance.

It is a further object of this invention to provide such a laminate having good abrasion resistance.

It is a still further object of the present invention to provide such a laminate that is inexpensive to produce.

It is also an object of the present invention to provide a novel process for producing such a laminate.

These and other objects will become apparent from the detailed description which follows.

The present invention provides a two-ply nonwoven fabric laminate comprising a first ply of synthetic fibrous nonwoven material having an outer surface, an inner surface, and a thickness, and having a basis weight of from about 10 g/m$^2$ to about 50 g/m$^2$; and a second ply of fibrous nonwoven material having an outer surface, an inner surface, and a thickness and having a basis weight of from about 10 g/m$^2$ to about 50 g/m$^2$. The laminate has a flexible, soft latex binder which adheres said inner surfaces of said first and second plies together. Said binder is adhered to substantially all fibers exposed on said inner surfaces of said first and second plies. Said binder is present in said first ply from said inner surface of said first ply to a depth of from about 20% to about 80% of said thickness of said first ply. Said binder is present in said second ply from said inner surface of said second ply to a depth of from about 20% to about 80% of said thickness of said second ply.

DETAILED DESCRIPTION OF THE INVENTION

The two-ply nonwoven fabric laminate of the present invention comprises a first ply of a synthetic fibrous nonwoven material and a second ply of a fibrous nonwoven material. The first ply of synthetic fibrous nonwoven material is preferably the ply which provides a majority of need strength to the two-ply nonwoven fabric laminate. Examples of synthetic fibrous nonwoven material suitable for use in the present invention include continuous-filament webs (especially spunbond webs), carded webs, randomized staple fiber webs, and the like. The fibrous nonwoven material second ply may be an airlaid or wetlaid cellulosic pulp sheet or any of the above-mentioned synthetic fibrous nonwoven materials. It is preferred that the second ply be an inexpensive ply which can supply bulk, softness, and cloth-like properties to the two-ply nonwoven fabric laminate. Based on these considerations, tissue is a preferred material for the fibrous nonwoven material second ply.

Figures 1, 2:
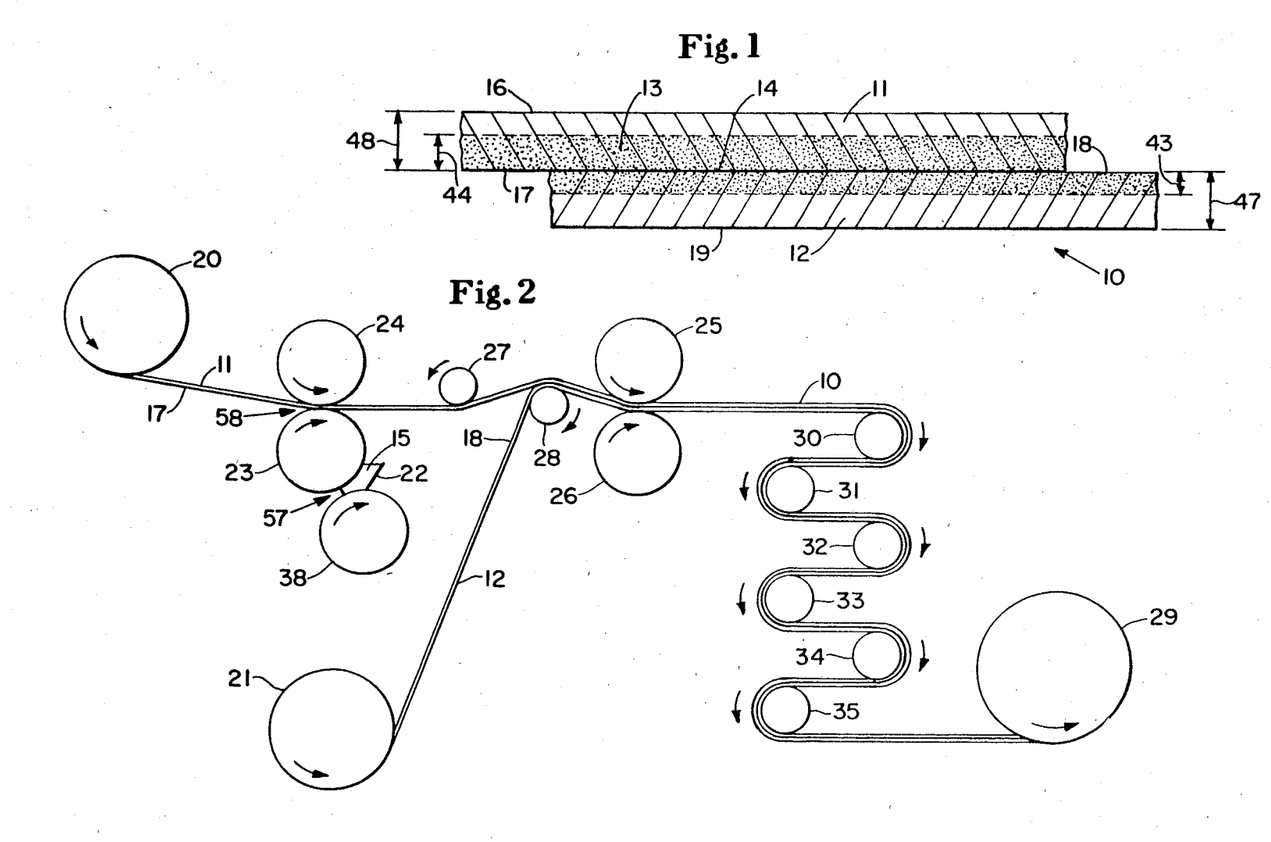
FIG. 1 is a semi-diagrammatic, fragmentary, cross-sectional view of a two-ply nonwoven fabric laminate of the present invention.
FIG. 2 is a schematic diagram of a preferred process for making the two-ply nonwoven fabric laminate of the present invention.

An exemplary laminate 10 of the present invention is illustrated in FIG. 1 as having two plies of material, spunbond web ply 11 and tissue ply 12. Spunbond web ply 11 has outer surface 16, inner surface 17, and thickness 48; tissue ply 12 has outer surface 19, inner surface 18, and thickness 47. Spunbond web ply 11 and tissue ply 12 have their respective inner surfaces 17 and 18 adhered together at interface 14 by latex binder 13, such that the outer surfaces 16 and 19 of respective plies 11 and 12 are also the outer surfaces of laminate 10.

Synthetic Fibrous Nonwoven Material

Spunbond web ply 11 is preferably a low tensile strength, low basis weight, no more than lightly bonded (may be substantially unbonded) layer of continuous-filament nonwoven material. The filament diameter of the spunbond web should be up to about 40 microns. Spunbond web ply 11 may be made from any polymer or polymer blend capable of being spun into a web, the most common being rayon, polyester, polypropylene or nylon. Spunbond polymers such as polyester, polypropylene and nylon are naturally hydrophobic. Spunbond polymers such as rayon are naturally hydrophilic. If a hydrophilic spunbond web is used, it may be treated to be hydrophobic, as is well known in the art.

Since spunbond webs are by virtue of their manufacturing process continuous-filament webs, they are naturally strong, abrasion resistant and lint free; this makes them especially suitable for surgical fabrics. Such webs can be appropriately colored and can be treated to be surface conductive and flame retardant if required.

The synthetic fibrous nonwoven materials used in the present invention preferably have a basis weight of from about 10 g/m$^2$ to about 50 g/m$^2$; more preferably from about 15 g/m$^2$ to about 30 g/m$^2$.

The synthetic fibrous nonwoven materials of the two-ply nonwoven fabric laminates of the present invention generally provide the primary tensile strength and tear resistance for the laminates. The composition, filament size, and basis weight of such materials are selected to provide adequate strength for the laminates.

Fibrous Nonwoven Material

Tissue ply 12 of the two-ply nonwoven fabric laminates of the present invention can be any conventional tissue and is selected to enhance the desired attributes of the laminates. Tissue ply 12 is preferably creped, or otherwise postworked in an equivalent manner, prior to combination in laminate 10. Due to the exemplary soft, bulky and absorbent features engendered therein, a particularly preferable tissue for use in laminate 10 is the paper tissue product disclosed and claimed in U.S. Pat. No. 3,301,746 issued to Sanford & Sisson on Jan. 31, 1967. The tissue product disclosed in this patent is characterized by having impressed in its surface, to a depth of at least 30% of its machine glazed caliper, the knuckle pattern of an imprinting fabric having from about 8 to about 24 meshes per centimeter, by having from about 1% to about 14% of its surface compressed in said knuckle patterns to a relative density of at least 0.7, and said tissue being further characterized by having a bulk density at 15.5 grams per square centimeter loading of from about 0.06 g/cm$^3$ to about 0.22 g/cm$^3$, proportional to its basis weight.

The basis weight of fibrous nonwoven materials, especially tissue, used in the present invention is preferably from about 10 g/m$^2$ to about 50 g/m$^2$; more preferably from about 15 g/m$^2$ to about 30 g/m$^2$.

Internal Latex Binder

The unique properties of the two-ply nonwoven fabric laminates of the present invention are achieved due, in part, to latex binder 13 used to bond the two plies, and the process used for applying binder 13 and bonding the plies together.

The prior art discloses many nonwoven fabric laminates where the binder used to adhere to plies together is applied in an intermittent pattern generally covering less than 30% of the surface area of the plies. Applicants have found that such an intermittent pattern of binder results in a relatively weak bond between the laminate plies which results in relatively easy delamination of the nonwoven fabric laminate. Consequently, it is preferred that latex binder 13 used to adhere plies 11 and 12 of laminate 10 be a substantially overall coating that adheres to substantially all the fibers (filaments) of spunbond web ply 11 exposed on inner surface 17 and to substantially all the fibers of tissue ply 12 exposed on inner surface 18 at interface 14 between said plies. This is achieved by providing a substantially continuous layer of latex binder emulsion at interface 14 during the process of manufacturing laminate 10. Such a continuous application of latex binder 13 also can result in improved tensile and tear strength and improved abrasion resistance of laminate 10; these properties are discussed in more detail hereinbelow.

The stated purpose for desiring an intermittent binder pattern, according to prior art references, is to avoid stiffness of the resulting fabric laminate which occurs with most binders when a substantially continuous binder application, such as that preferred for laminates of the present invention, is employed. Such stiffness is avoided in laminates of the present invention by using a latex binder that remains flexible and soft after it dries. A latex binder having a glass transition temperature of from about 0° C. to about −80° C., preferably from about −20° C. to about −40° C., can provide such properties. Latex binders with such low glass transition temperatures remain tacky at room temperature. Because of this tackiness, it is important that binder 13 not be present on outer surfaces 16 and 19 of two-ply nonwoven fabric laminate 10, since the presence of a tacky binder on outer surface 16 and/or 19 could cause laminate 10 to stick to other materials with which it comes in contact.

Examples of latex binders suitable for use in the present invention are polymers and copolymers of acrylate esters, referred to generally as acrylic polymers, vinyl acetate-ethylene copolymers, styrene-butadiene copolymers, vinyl chloride polymers, vinylidene chloride polymers, vinyl chloride-vinylidene chloride copolymers, acrylo-nitrile copolymers, and acrylic-ethylene copolymers. The water emulsions of these latex binders usually contain surfactants; preferably, the surfactants are modified during drying and curing so that they become incapable of rewetting.

Of the latex binders enumerated, the acrylic polymer types are highly preferred. Examples of acrylic polymer water emulsions suitable for use in the present invention are available from the Rohm & Haas Company under the designations E-920 and HA-8, from the Union Carbide Corporation under the designation BX-3006, and from the Union Oil Company of California under the tradename Amsco-Res 6320.

Latex binder 13 is applied in the form of an aqueous emulsion 15. Emulsion 15 is kept from penetrating entirely through plies 11 and 12 to outer surfaces 16 and 19 of two-ply nonwoven fabric laminate 10 by using an emulsion having high viscosity and solids content, by the method of applying emulsion 15 to laminate plies 11 and 12, and by the process used to adhere plies 11 and 12 together. Although the present invention is not limited to any particular theory, the ways in which applicants believe these variables affect penetration of plies 11 and 12 by latex binder emulsion 15 are presented hereinbelow. Penetration of emulsion 15 is generally presented as a percent of thicknesses 48 and 47 of plies 11 and 12, respectively, through which emulsion 15 has migrated; such percentages are averages taken across the surface area of two-ply fabric laminate 10.

Because the fibrous nonwoven ply, e.g. tissue ply 12, is generally water absorbent, aqueous latex binder emulsion 15 tends to be absorbed by such ply. Penetration of tissue ply 12 is controlled primarily by using an emulsion having a high solids content; this effectively limits the depth to which latex binder emulsion 15 is absorbed into tissue ply 12. Some penetration of emulsion 15 into tissue ply 12 is needed in order to bind most of the fibers of tissue ply 12 so that they are not easily abraided from outer surface 19 of two-ply nonwoven fabric laminate 10.

Excess penetration of tissue ply 12 by latex binder emulsion 15 not only results in a tacky outer surface 19, but also interferes with waterproofing of two-ply nonwoven fabric laminate 10. Waterproofing of laminate 10 is achieved after lamination by the addition of waterproofing chemicals which are absorbed primarily by tissue ply 12, thus making laminate 10 water and alcohol repellent.

A minimum penetration of about 20% of thickness 47 of tissue ply 12 from inner surface 18 by latex binder emulsion 15 is needed in order to achieve good fabric integrity; but a penetration of at least about 50% of thickness 47 of tissue ply 12 is preferred in order to also obtain better abrasion resistance of outer surface 19 of laminate 10. If penetration of emulsion 15 is greater than about 80% of thickness 47 of tissue ply 12, spots are likely to occur where latex binder 13 has reached surface 19 of tissue ply 12. Thus, after emulsion 15 dries, the desired penetration of emulsion 15 results in latex binder 13 being present in tissue ply 12 from inner surface 18 to a depth 43 of from about 20% to about 80% of thickness 47 of tissue ply 12, preferably from about 50% to about 80% of said thickness.

The synthetic fibrous nonwoven material ply, e.g. spunbond web ply 11, used in two-ply nonwoven fabric laminate 10 is often a hydrophobic material which has little tendency to absorb aqueous latex binder emulsion 15. The degree of penetration of a hydrophobic ply is controlled primarily by the viscosity of emulsion 15. If the synthetic fibrous nonwoven material is hydrophilic, the degree of penetration of that ply may be more affected by solids content of emulsion 15, similar to tissue ply 12.

The filaments of spunbond web ply 11 are preferably no more than lightly bonded toghether (they may be substantially unbonded) prior to lamination so that spunbond web ply 11 is soft, nonbrittle, and flexible. Such a web has little tensile strength due to the lack of bonding between most filaments. Impregnation of spunbond web ply 11 by latex binder 13 provides a flexible bonding agent between the filaments which enhances the tensile strength of spunbond web ply 11 while retaining its softness and flexibility. This flexible bonding of the filaments of spunbond web ply 11 also results in two-ply nonwoven fabric laminate 10 having high tear strength, since the filaments are not rigidly adhered together, but instead have some freedom to move relative to each other.

A minimum penetration of latex binder emulsion 15 into spunbond web ply 11 from inner surface 17 of at least about 20% of thickness 48 of spunbond web ply 11 is needed in order to achieve good fabric integrity; but a penetration of at least about 50% of thickness 48 of spunbond web ply 11 is preferred, when spunbond web ply 11 is no more than lightly bonded, to achieve sufficient binding of its filaments to provide the desired tensile and tear strength of laminate 10. If penetration of emulsion 15 is greater than about 80% of the thickness of spunbond web ply 11, spots are likely to occur where latex binder 13 has reached outer surface 16 of spunbond web ply 11. Thus, after emulsion 15 dries, the desired penetration of emulsion 15 results in latex binder 13 being present in spunbond web ply 11 from inner surface 17 to a depth 44 of from about 20% to about 80% of thickness 48 of spunbond web ply 11, preferably from about 50% to about 80% of said thickness.

Aqueous latex binder emulsion 15 used to produce two-ply nonwoven fabric laminate 10 can provide the balance of properties specified hereinabove when emulsions of the preferred acrylic polymers have a solids content in the range of from about 45% to about 80%, preferably from about 55% to about 70%, and a viscosity of from about 8,000 cp to about 25,000 cp, preferably from about 12,000 cp to about 20,000 cp, more preferably from about 14,000 cp to about 17,000 cp (Brookfield viscosity with a No. 2 spindle, 6 rpm). When applied to the inner surface(s) 17 and/or 18 of one or both of plies 11 and 12, a substantial portion of latex binder emulsion 15 with such high solids content and viscosity will remain at interface 14 between inner surfaces 17 and 18 of spunbond web ply 11 and tissue ply 12, respectively, thus providing a laminate which is resistant to delamination. However, if too much of latex binder 13 were to be present at interface 14 between plies 11 and 12, it could be in the form of a cohesive film, and the resulting fabric laminate would have a very low air porosity. The quantity (solids basis) of latex binder 13 present in two-ply nonwoven fabric laminate 10 is preferably from about 5 $g/m^2$ to about 20 $g/m^2$, more preferably from about 7 $g/m^2$ to about 15 $g/m^2$, most preferably from about 8 $g/m^2$ to about 12 $g/m^2$.

The examples of acrylic polymer water emulsions suitable for use in the present invention specified hereinabove are available within the solids content ranges specified hereinabove. Such emulsions are generally available at low pH (e.g. about 2-3) and at viscosities much lower than specified hereinabove. The viscosity of such acrylic polymer emulsions can often be increased to the desired level by raising the pH of the emulsion. The preferred additive for raising the pH of the acrylic polymer emulsion to achieve the desired viscosity is an aqueous ammonia solution containing about 10% $NH_3$. An addition of about about 1–3% of such aqueous ammonia solution to an acrylic polymer emulsion will generally result in an emulsion having the desired viscosity.

If the desired viscosity of the acrylic polymer emulsion is not achieved solely by pH adjustment, various thickeners can be used in order to achieve the desired viscosity. Preferred thickeners are acrylic emulsion copolymers of polyacrylic acid or polymethacrylic acid. An example of such a thickener is available from the Rohm & Haas Company under the designation Acrysol ASE-75, an acrylic emulsion copolymer containing 38–41% solids and having a pH of about 2½. The Acrysol ASE-75 is added to the acrylic polymer latex binder at a level of from about ¼% to about 2% (solids/-solids basis). Ten percent aqueous ammonia solution is then blended with the binder-thickener blend until the desired viscosity is achieved.

Other thickeners that may be used to provide the desired viscosity of the acrylic polymer binder emulsions include sodium polyacrylate or sodium polymethyacrylate and mixtures thereof. Such a thickener is available from the Union Oil Company of California under the tradename Amsco-Res 8306.

Other conventinal thickeners which are well known in the art may be used to thicken the latex binder emulsions of the present invention; examples of such thickeners include methylcellulose, carboxymethylcellulose, ethylcellulose, and the like.

Method Of Manufacture

FIG. 2 is a schematic diagram of a preferred process for making the two-ply nonwoven fabric laminates of the present invention. Supply rolls of spunbond web ply 11 and tissue ply 12 are rolls 20 and 21, respectively. A high viscosity, high solids content latex binder emulsion 15, as specified hereinabove, is applied to the inner surface of the spunbond web ply or the tissue ply or to the inner surfaces of both plies; the emulsion is preferably applied by applicator roll 23 to inner surface 17 of spunbond web ply 11. Spunbond web ply 11 travels under idler roll 27 and is brought in contact with tissue ply 12 as both are brought over idler roll 28, which is preferably a bowed roll. Thus inner surface 17 of spunbond web ply 11 to which latex binder emulsion 15 has been applied contacts inner surface 18 of tissue ply 12. The laminate of spunbond web ply 11 and tissue ply 12 is then compressed under low pressure by passing it through the nip of smooth, combiner rolls 25 and 26, thus producing two-ply nonwoven fabric laminate 10. The pressure provided by combiner rolls 25 and 26 on plies 11 and 12 is high enough to cause substantially the entire inner surfaces 17 and 18 of spunbond web ply 11 and tissue ply 12 to be adhered together, but is low enough to avoid squeezing latex binder emulsion 15 entirely through either of plies 11 or 12 of two-ply nonwoven fabric laminate 10.

Resulting two-ply nonwoven fabric laminate 10 is next contacted with the surface of heated rolls 30, 31, 32, 33, 34 and 35 in order to cure and dry latex binder emulsion 15 within nonwoven fabric laminate 10. The temperatures of the surfaces of heated rolls 30, 31, 32, 33, 34 and 35 is preferably kept below about 160° C. to avoid deformation of spunbond web ply 11. Two-ply nonwoven fabric laminate 10 is then wound onto takeup roll 29 for storage, or may be taken directly to further processing steps to soften and/or waterproof laminate 10.

Figure 3:
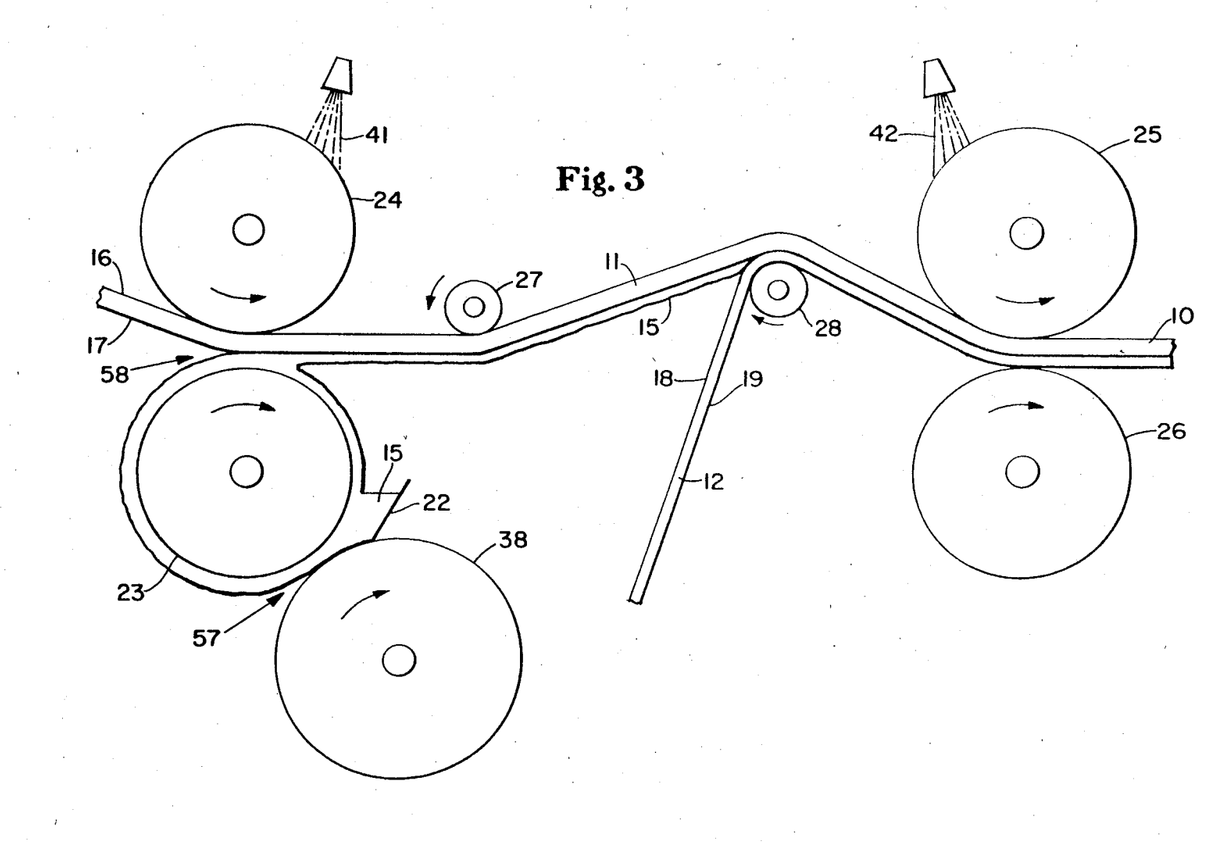
FIG. 3 is an enlarged schematic diagram of the latex applicator and ply combining portions of the process shown in FIG. 2.

FIG. 3 provides a detailed schematic view of a preferred latex application and ply combining steps of the process shown in FIG. 2. Latex binder emulsion 15 is contained in trough 22 such that emulsion 15 is in contact with applicator roll 23. The surface of applicator roll 23, which is preferably smooth, thus becomes coated with emulsion 15; the thickness of the coating of emulsion 15 on applicator roll 23 is controlled by metering roll gap 57 between applicator roll 23 and metering roll 38 which rotates in a direction such that its surface is travelling in the opposite direction of that of applicator roll 23 at gap 57.

Inner surface 17 of spunbond web ply 11 is forced by backup roll 24 to contact latex binder emulsion 15 on the surface of applicator roll 23. Applicator roll gap 58 between backup roll 24 and applicator roll 23 is controlled such that emulsion 15 is applied to inner surface 17 of spunbond web ply 11, but such that emulsion 15 is not squeezed through ply 11; this surface application of emulsion 15 is termed "kiss-coating". A fine waterspray 41 may be sprayed onto the surface of backup roll 24 to keep its surface moist; this prevents any latex binder emulsion 15 that might come in contact with the surface of roll 24 from drying on the roll surface and causing spunbond web ply 11 to stick to the surface of roll 24.

Spunbond web ply 11 then travels under idler roll 27 which ensures that spunbond web ply 11 is taught as it travels over bowed roll 28. Tissue ply 12 also travels over bowed roll 28 where its inner surface 18 contacts inner surface 17 of spunbond web ply 11 to which latex binder emulsion 15 has been applied, thus plies 11 and 12 are adhered together. Resulting two-ply nonwoven fabric laminate 10 travels through the nip of combiner rolls 25 and 26 under low pressure to ensure that there is substantially complete contact between inner surfaces 17 and 18 of spunbond web ply 11 and tissue ply 12 while avoiding squeezing emulsion 15 entirely through either ply. Fine waterspray 42 may be used to keep the surface of roll 25 moist so that if any latex binder emulsion 15 should come in contact with its surface, the binder will not dry on the roll surface and cause two-ply fabric laminate 10 to stick to the surface of roll 25.

When a two-ply nonwoven fabric laminate of the present invention is to be used as a surgical fabric, it is preferably treated in order to reduce fiber linting from the outer tissue surface of the laminate and also to made the laminate water repellent. A common method for reducing linting of such laminates is to treat at least outer tissue surface 19 of the laminate with an external binder system. The nonwoven fabric laminate is made water repellent by treatment with waterproofing chemicals.

While a wide variety of adhesives such as solid adhesives, hot melt adhesives, and adhesives dispersed in organic solvent can be applied as external binders to reduce linting, a preferred external binder system for reducing linting of the two-ply nonwoven fabric laminates of the present invention is a latex binder applied as an aqueous emulsion into which the laminate is immersed. The two-ply nonwoven fabric laminate is then removed from the latex binder emulsion bath and dried before further processing. An alternative preferred method for applying the external binder system is to apply it as a concentrated emulsion by printing on outer tissue surface 19 of two-ply nonwoven fabric laminate 10. Latex adhesives such as ethylene-vinyl acetate latexes, acrylic latexes, styrene-butadiene rubber latexes, or other emulsifiable latex adhesives are preferred; especially preferred are ethylene-vinyl acetate latexes. Ethylene-vinyl acetate latex emulsions which are preferred have a nonionic surfactant, a latex solids content between 45% and 55%, a viscosity between 700 cp and 1200 cp (Brookfield viscosity with a No. 3 spindle, 60 rpm), and a pH between 5.0 and 6.0. Such latex emulsions are available commercially from Air Products & Chemicals, Inc., under the Tradename Airflex.

The external binder latex emulsions are preferably dispersed in additional water; the preferred concentration range for external binder latexes in aqueous emulsions to be applied to nonwoven fabrics is from about 1% to about 30%. For the fabric immersion process, the preferred latex concentration in the emulsion is between about 1% and about 5%; the preferred concentration range of the latex is from about 10% to about 30% for the printing process. The quantity of external binder (solids basis) added to the fabric is preferably from about 0.4 $g/m^2$ to about 4 $g/m^2$, from about 0.5 $g/m^2$ to about 1 $g/m^2$ is especially preferred. At this low level of addition, the external binder prevents linting from the tissue ply of the two-ply nonwoven fabric laminate, but does not significantly interfere with the absorption of waterproofing chemicals by the tissue ply.

Any of a wide variety of waterproofing treatments can be utilized for the two-ply nonwoven fabric laminates of the present invention. The nonwoven fabric laminates are preferably immersed in a waterproofing emulsion and then dried. The preferred waterproofing treatments include aqueous emulsions of waxes, resins, silicone compounds, fluorochemical compounds, and mixtures thereof; especially preferred are aqueous emulsions containing a combination of a fluorochemical and a wax or resin extender.

Fluorochemicals used include straight chain, highly fluorinated hydrocarbons. Examples of preferred fluorochemical treatments include emulsions of fluorochemical polymers with a solids content of from about 20% to about 45%. Such treatments are available commercially from E. I. Du Pont de Nemours & Co., Inc. under the Tradename ZONYL and from 3M Company under the Tradename SCOTCHBAN.

A preferred resin extender is a 100% solids waxy chip of triazine resin which is emulsified with hot water and an acid catalyst (pH about 2.2), having aluminum glycolate as its active ingredient. Such an extender is Phobotex FTC supplied by Ciba-Geigy Corporation. An antifoam agent is often included in such resin formulations; for example, silicone antifoam agents such as AF-71 available commercially from the General Electric Company.

Waxes used include parafinic waxes, examples are available commercially from E. I. Du Pont de Nemours & Co., Inc. The waxes are emulsified in water by the addition of a nonionic surfactant. Mixtures of waxes and resins may also be used as extenders.

The waterproofing chemicals are preferably incorporated in an aqueous emulsion at a solids concentration ranging from about 0.1% to about 7%. For the especially preferred combination of fluorochemical and extender, the preferred solids concentrations are from about 0.1% to about 0.5% fluorochemical, and from about 0.4% to about 1% extender. The quantity of waterproofing compounds (solids basis) incorporated in the laminate are preferably from about 0.05 $g/m^2$ to about 2 $g/m^2$ fluorochemical and from about 0.2 $g/m^2$ to about 5 $g/m^2$ extender; especially preferred is from about 0.1 $g/m^2$ to about 0.5 $g/m^2$ fluorochemical and from about 0.5 $g/m^2$ to about 1 $g/m^2$ extender.

The waterproofed two-ply nonwoven fabric laminates of the present invention preferably have a liquid strikethrough resistance of greater than about 180 mm $H_2O$, more preferably greater than about 200 mm $H_2O$, and an air porosity of preferably greater than about 200 $l/sec/m^2$, more preferably greater tha about 250 $l/sec/m^2$. A basis weight of said laminate of no more than about 85 $g/m^2$ is preferred; a basis weight of no more than about 70 $g/m^2$ is more preferred; a basis weight of no more than about 60 $g/m^2$ is especially preferred.

After drying, the two-ply nonwoven fabric laminates of the present invention are preferably accorded a mechanical postworking treatment to fully develop and enhance the cloth-like aesthetic properties of the laminate. Mechanical postworking treatments preferably involve compaction which results in microcreping of the laminates. Mechanical compaction treatments resulting in from about about 1% to about 30%, preferably from about 4% to about 20%, compaction have been found desirable and such treatments can be advantageously applied repetitively with intermittent or subsequent pullout of substantial amounts of the compaction. Exemplary mechanical compaction systems are disclosed in U.S. Pat. Nos. 2,624,245 issued to Cluett on Jan. 6, 1953; 3,260,776 issued to Walton on July 12, 1966; 3,426,405 issued to Walton on Feb. 11, 1969; and 4,090,385 issued to Packard on May 23, 1978.

TEST PROCEDURES

The test procedures used to determine the properties of the two-ply nonwoven fabric laminates of the present invention and to provide the test results in the examples below are as follows:

Air Porosity Test

The test for air porosity of the nowoven fabric laminates conforms to ASTM test method D-737, with the exception that the material to be tested is conditioned at 23° C.±1° C. and 50%±2% relative humidity for a minimum of 12 hours prior to testing. The air porosity is reported as liters per second per square meter at 12.7 mm $H_2O$ differential pressure. A high volume is desired.

Liquid Column Strikethrough Resistance Test

The liquid strikethrough resistance test is a method for determining the water pressure in millimeters of water at which water penetrates a nonwoven fabric laminate at a specified fill rate and with the water and laminate at a specified temperature.

The strikethrough tester comprises a vertically mounted clear plastic tube with an inside diameter of 50.8 mm±1.6 mm having a flange on the bottom of the tube with rubber gaskets to hold the samples. Each sample consists of at least five individual test specimens cut to 90 mm×90 mm.

Each test specimen is appropriately affixed to the bottom of the tube with its tissue side up. Water is introduced into the tube at a filling rate of 6.7 cc per second giving a rate increase of water pressure of 3.3 mm of water per second. Both the water and the nonwoven fabric laminate are conditioned to 23° C.±1° C. When the first drop of water penetrates the sample specimen, the column height is read for that specimen in millimeters of water. The liquid column strikethrough resistance value for each sample is an average of the values of the five specimens for that sample. A high value is desired.

Tensile Strength Test

A 2.5 cm wide strip of the fabric laminate for which tensile strength is to be determined is tested in an Instron Table Model EM with a tension load cell "C" (range 4.4–22.2 newtons). An initial jaw spacing of 5.1 cm is used together with a crosshead speed of 5.1 cm per minute. The tensile strength is reported as tensile to break in newtons per meter. Tensile strength can be measured in the machine direction (MD) of the laminate or in the cross-machine direction (CD). A high value is desired.

Tear Strength Test

Tear strength is determined using an Elmendorf Tearing Tester and ASTM Test Method D-1424, with the exception the sample is conditioned at 23° C.±1° C. and a relative humidity of 50%±2% for 12 hours. Tear strength can be measured in the machine direction (MD) of the laminate or in the cross-machine direction (CD). The value is reported in grams, and a high value is desired.

Abrasion Resistance Test

Samples of fabric laminate to be tested are cut into 15 cm×15 cm squares with a 1.3 cm diameter hole cut in the center. Each sample is placed in a weighing bottle and dried in an oven at 110° C. for 2 hours. The temperature and drying time may be adjusted for different types of fabrics. After removing the samples from the oven, they are placed in a dessicator and are allowed to cool to room temperature (approximately 1 hour).

The saples are then weighed to the nearest 0.0001 gram. Each sample is then placed on a Taber abraser-Research Model and the weight is set to a 125 gram load per wheel. CS-8 wheels are used. The abraser is run the number of cycles desired, normally one hundred. The wheels are then lifted and the sample is brushed, making sure that all non-attached particles are removed. The particles which are loosely attached to the fabric remain. The wheels and table are dried and brushed to remove any clinging particles. Each sample is again placed in a weighing bottle and completely dried in an oven (the time and temperature being adjusted according to the fabric being tested). After each sample is removed from the oven and cooled to room temperature, it is again weighed and recorded, and the weight loss in milligrams is computed. A low number is desired.

EXAMPLES

The following examples will illustrate the invention, but are not intended to be any way limiting thereof.

Example 1

A two-ply nonwoven fabric laminate was made by the process shown in FIGS. 2 and 3 and described hereinabove. The tissue used was a soft, bulky and absorbent tissue made according to the teachings of U.S. Pat. No. 3,301,746 as disclosed hereinabove; the tissue ply had a basis weight of about 24 g/m$^2$. The spunbond web was Reemay T-387 supplied by E. I. Du Pont de Nemours & Company, Inc., a polyester web having a basis weight of about 19 g/m$^2$ and a fiber diameter of about 12–16 μm.

The latex binder used was Amsco-Res 6320 having a solids content of about 65%, a viscosity of about 1500 cp, and a pH of about 2; its viscosity was adjusted to about 13,500 cp by the addition of aqueous ammonia (10%) solution.

The process was run at a line speed of about 91 m/min. Metering roll gap 57 was set at about 0.08 mm and applicator roll gap 58 was adjusted to achieve a pickup of latex binder emulsion of about 16 g/m$^2$ (about 10 g/m$^2$ solids basis) on the spunbond web. The nip pressure between combiner rolls 25 and 26 was adjusted to about 3.6 kg/cm. Seam was fed to drying rolls 30, 31, 32, 33, 34 and 35 to maintain their temperatures at about 150° C.

The resulting two-ply nonwoven fabric laminate was subsequently treated with an external binder system to reduce fiber linting by printing on the tissue side with an emulsion of Airflex A120 containing about 18% solids. The pickup of external binder (solids basis) was bout 0.7 g/m$^2$ of fabric laminate. The fabric laminate was then dried. A waterproofing treatment was applied to the fabric laminate by dipping into a bath containing about 0.5% Scotchban FC-824 and about 1.0% Phobotex FTC (solids bases). The treated two-ply fabric laminate was then dried at about 173° C., resulting in the fabric laminate having incorporated in it about 0.3 g/m$^2$ Scotchban FC-824 and about 0.6 g/m$^2$ Phobotex FTC (solids bases).

The physical properties of the resulting two-ply nonwoven fabric laminate are shown in the Table below.

Example 2

A two-ply nonwoven fabric laminate was made by the same process as the laminate in Example 1. The tissue ply was the same as that used in Example 1. The spunbond web ply was a polyester web, E1030, produced by Asahi Chemical Industry Company Ltd. of Osaka, Japan; it had a basis weight of about 29 g/m$^2$ and a fiber diameter of about 10–12 μm. Amsco-Res 6320 was used as the latex binder and its viscosity was adjusted to 18,600 cp by the addition of aqueous ammonia (10%) solution.

The process was run at a line speed of about 78 m/min., and the applicator roll gap was adjusted to achieve a latex binder pickup of about 22 g/m$^2$ (about 14 g/m$^2$ solids basis) on the spunbond web. Other variables in the laminating process were the same as for Example 1.

The resulting two-ply nonwoven fabric laminate was subsequently treated with an external binder system by printing on the tissue side with an emulsion of Airflex A120 containing about 21% solids. The fabric laminate was then dried. A waterproofing treatment was applied to the fabric laminate by dipping into a bath containing about 0.5% Scotchban FC-824 an about 0.9% Phobotex FTC (solid bases). The treated two-ply fabric laminate was then dried at about 173° C. The pickup of external binder solids and waterproofing solids was not measured.

The physical properties of the resulting two-ply nonwoven fabric laminate are shown in the Table below.

Example 3

A two-ply nonwoven fabric laminate was made by the same process as the laminate in Example 1. The tissue ply was the same as that used in Example 1. The spunbond web ply was a nylon web, N3030, produced by Ashi Chemical Industry Company Ltd. and having a basis weight of about 29 g/m$^2$ and a fiber diameter of about 12-15 μm. Amsco-Res 6320 was used as the latex binder and its viscosity was adjusted to 17,000 cp by the addition of aqueous ammonia (10%) solution.

The process was run at a line speed of about 91 m/min. Applicator roll gap 58 was adjusted to achieve a latex binder pickup of about 30g/m$^2$ (about 19 g/m$^2$ solids basis) on the spunbond web. The other variables in the fabric making process were the same as for Example 1.

The resulting two-ply nonwoven fabric laminate was subsequently treated with an external binder system by printing on the tissue side with an emulsion of Airflex A120 containing about 18% solids. The pickup of external binder (solids bases) was about 0.7 g/m$^2$ of fabric laminate. The fabric laminate was then dried. A waterproofing treatment was applied to the fabric laminate by dipping into a bath containing about 0.4% Scotchban FC-824 and about 1.0% Phobotex FTC (solids bases). The treated two-ply fabric laminate was then dried at about 173° C., resulting in the fabric laminate having incorporated in it about 0.3 g/m$^2$ Scotchban FC-824 and about 0.7 g/m$^2$ Phobotex FTC (solids bases).

Example 4

A two-ply nonwoven fabric laminate was made by the same process as the laminate in Example 1. The tissue ply was the same as that used in Example 1. The spunbond web ply was a nylon web, N3030, produced by Asahi Chemical Industry Company Ltd. and having a basis weight of about 29 g/m$^2$ and a fiber diameter of about 12-15 μm. Amsco-Res 6320 was used as the latex binder and its viscosity was adjusted to 15,000 cp by the addition of aqueous ammonia (10%) solution.

The process was run at a line speed of about 182 m/min. Applicator roll gap 58 was adjusted to achieve a latex binder pickup of about 15 g/m$^2$ solids basis) on the spunbond web. The other variables in the fabric making process were the same as for Example 1.

The resulting two-ply nonwoven fabric laminate was subsequently treated with an external binder system and waterproofing system the same as the laminate of Example 3.

The physical properties of the resulting two-ply nonwoven fabric laminate are shown in the Table below.

TABLE

| Physical Property Of Laminate | Example 1 | Example 2 | Example 3 | Example 4 |
|---|---|---|---|---|
| Basis Weight (g/m$^2$) | 55 | 69 | 74 | 66 |
| Air Porosity (l/sec/m$^2$) | 280 | 210 | 290 | 260 |
| Liquid Column Strike-through (mm H$_2$O) | 190 | 250 | 210 | 240 |
| Tensile Strength MD (newtons/m) CD | 90 | 260 | 260 | 230 |
|  | 80 | 150 | 90 | 90 |
| Tear Strength (g) MD | 350 | 490 | 1090 | 640 |
| Abrasion (mg) | 24 | 11 | 11 | — |

While particular embodiments of the present invention have been illustrated and described, those skilled in the art will recognize that various changes and modifications can be made without departing from the spirit and scope of the invention. It is intended to cover, in the appended claims, all such modifications that are within the scope of this invention.

What is claimed is:

1. A process for making a two-ply nonwoven fabric laminate having a first ply of synthetic fibrous nonwoven material having an outer surface, an inner surface, and a thickness and a second ply of fibrous nonwoven material having an outer surface, an inner surface, and a thickness comprising:
   (a) coating said inner surface(s) of at least one of said first and second plies with a substantially continuous layer of an aqueous emulsion of a flexible, soft latex binder, said emulsion having a solids content of from about 45% to about 80% and a viscosity of from about 8,000 cp to about 25,000 cp, said latex binder having a glass transition temperature of from about 0° C. to about −80° C.;
   (b) forming said two-ply laminate by adhering said inner surfaces of said first ply and said second ply together under pressure, whereby said emulsion penetrates from said inner surface of said first ply to a depth of from about 20% to about 80% of said thickness of said first ply, and said emulsion penetrates from said inner surface of said second ply to a depth of from about 20% to about 80% of said thickness of said second ply; and
   (c) drying said emulsion.

2. The process of claim 1 wherein said second ply is tissue.

3. The process of claim 2 wherein said latex binder is an acrylic polymer binder.

4. The process of claim 3 wherein said first ply is a spunbond web.

5. The process of claim 4 wherein said spunbond web is no more than lightly bonded, and said emulsion penetrates from said inner surface of said first ply to a depth of from about 50% to about 80% of said thickness of said first ply.

6. The process of claim 3 wherein said first ply has a basis weight of from about 10 g/m$^2$ to about 50 g/m$^2$, said second ply has a basis weight of from about 10 g/m$^2$ to about 50 g/m$^2$, and said emulsion is coated on said inner surface(s) in an amount of from about 5 g/m$^2$ to about 20 g/m$^2$ (solids basis).

7. The process of claim 5 wherein said first ply has a basis weight of from about 10 g/m$^2$ to about 50 g/m$^2$, said second ply has a basis weight of from about 10 g/m$^2$ to about 50 g/m$^2$, and said emulsion is coated on said inner surface(s) in an amount of from about 7 g/m$^2$ to about 15 g/m$^2$ (solids basis).

8. The process of claim 6 wherein said emulsion penetrates from said inner surface of said second ply to a depth of from about 50% to about 80% of said thickness of said second ply.

9. The process of claim 7 wherein said emulsion penetrates from said inner surface of said second ply to a depth of from about 50% to about 80% of said thickness of said second ply.

10. The process of claim 8 wherein said emulsion has a solids content of from about 55% to about 70%.

11. The process of claim 9 wherein said emulsion has a solids content of from about 55% to about 70%.

12. The process of claim 10 wherein said emulsion has a viscosity of from about 12,000 cp to about 20,000 cp.

13. The process of claim 11 wherein said emulsion has a viscosity of from about 12,000 cp to about 20,000 cp.

14. The process of claim 12 wherein said binder has a glass transition temperature of from about −20° C. to about −40° C.

15. The process of claim 13 wherein said binder has a glass transition temperature of from about −20° C. to about −40° C.

16. The process of claim 15 wherein said emulsion has a viscosity of from about 14,000 cp to about 17,000 cp, and said emulsion is coated on said inner surface(s) in an amount of from about 8 g/m$^2$ to about 12 g/m$^2$ (solids basis).

17. The process of claim 15 wherein said process also comprises:
  (d) applying waterproofing chemicals to said two-ply laminate; and
  (e) drying said twoply laminate.

18. The process of claim 17 wherein an external binder system is applied at least to said outer surface of said second ply after step (c).

19. A process for making a two-ply nonwoven fabric laminate having a first ply of continuous-filament spunbond web having an outer surface and an inner surface, and a second ply of tissue having an outer surface and an inner surface comprising:
  (a) kiss-coating said inner surface(s) of at least one of said first and second piles with an aqueous emulsion of a flexible, soft acrylic polymer binder, said emulsion having a solids content of from about 45% to about 80% and a viscosity of from about 8,000 cp to about 25,000 cp, said latex binder having a glass transition temperature of from about 0° C. to about −80° C.;
  (b) forming said two-ply laminate by adhering said inner surfaces of said first ply and said second ply together under low pressure, whereby said latex binder penetrates from said inner surfaces of said first and second plies into said first and second plies but not to said outer surface of either said first ply or said second ply;
  (c) drying said emulsion;
  (d) applying waterproofing chemicals to said two-ply laminate; and
  (e) drying said two-ply laminate.

20. The process of claim 19 wherein said first ply has a basis weight of from about 10 g/m$^2$ to about 50 g/m$^2$, said second ply has a basis weight of from about 10 g/m$^2$ to about 50 g/m$^2$, and said emulsion is coated on said inner surface(s) in an amount of from about 5 g/m$^2$ to about 20 g/m$^2$ (solids basis).

21. The process of claim 19 wherein said first ply has a basis weight of from about 15 g/m$^2$ to about 30 g/m$^2$; said second ply has a basis weight of from about 15 g/m$^2$ to about 30 g/m$^2$; said emulsion has a solids content of from about 55% to about 70%, a viscosity of from about 12,000 cp to about 20,000 cp, and is coated on said inner surface(s) in an amount of from about 7 g/m$^2$ to about 15 g/m$^2$ (solids basis); and said latex binder has a glass transition temperature of from about −20° C. to about −40° C.

22. The process of claim 21 wherein an external binder system is applied at least to said outer surface of said second ply after step (c).

* * * * *

UNITED STATES PATENT AND TRADEMARK OFFICE
CERTIFICATE OF CORRECTION

PATENT NO.  : 4,588,457
DATED       : May 13, 1986
INVENTOR(S) : Susan L. H. Crenshaw, et. al.

It is certified that error appears in the above-identified patent and that said Letters Patent is hereby corrected as shown below:

Column 1, at line 33:   delete "are" and insert --where--

Column 1, at line 34:   delete "resistance," and insert --resistance--

Column 2, at line 23:   delete "Jan. 29" and insert --Jan. 28--

Column 3, at line 20:   delete "need" and insert --needed--

Column 10, at line 31:  delete "tha" and insert --than--

Column 11, at line 30:  delete "EM" and insert --TM--

Column 11, at line 58:  delete "saples" and insert --samples--.

Column 13, at line 22:  delete "Ashi" and insert --Asahi--.

Column 13, at line 60:  delete "about 15 g/m$^2$ solids basis)" and insert --about 15 g/m$^2$ (about 10 g/m$^2$ solids basis)--

Column 15, at line 35:  delete "twoply" and insert --two-ply--

Signed and Sealed this

Fourteenth Day of October, 1986

[SEAL]

Attest:

DONALD J. QUIGG

Attesting Officer

Commissioner of Patents and Trademarks